(12) United States Patent
Sanchez et al.

(10) Patent No.: US 7,557,710 B2
(45) Date of Patent: Jul. 7, 2009

(54) SYSTEM FOR TRACKING SURGICAL ITEMS IN AN OPERATING ROOM ENVIRONMENT

(75) Inventors: Michael Sanchez, Helotes, TX (US); James Parker, San Antonio, TX (US); James Ross, Montgomery Village, MD (US); Charles Beason, San Antonio, TX (US); Thomas Dayton, San Antonio, TX (US)

(73) Assignee: Med Wave, LLC, San Antonio, TX (US)

( * ) Notice: Subject to any disclaimer, the term of this patent is extended or adjusted under 35 U.S.C. 154(b) by 297 days.

(21) Appl. No.: 11/646,170

(22) Filed: Dec. 27, 2006

(65) Prior Publication Data

US 2007/0268133 A1 Nov. 22, 2007

Related U.S. Application Data

(60) Provisional application No. 60/783,096, filed on Mar. 17, 2006.

(51) Int. Cl.
G08B 13/14 (2006.01)
G08B 5/22 (2006.01)
G08B 1/08 (2006.01)
G06F 19/00 (2006.01)
G06F 7/00 (2006.01)

(52) U.S. Cl. .............. 340/572.1; 340/5.92; 340/825.49; 340/539.13; 235/385; 700/215

(58) Field of Classification Search ... 340/572.1–572.9, 340/5.92, 825.49, 539.13; 235/385; 700/215, 700/224, 225, 226
See application file for complete search history.

(56) References Cited

U.S. PATENT DOCUMENTS

| 3,097,649 A | 7/1963 | Gray |
| 3,834,390 A | 9/1974 | Hirsch |
| 4,114,601 A | 9/1978 | Abels |
| 4,193,405 A | 3/1980 | Abels |
| 4,658,818 A | 4/1987 | Miller, Jr. et al. |
| 5,107,862 A | 4/1992 | Fabian et al. |
| 5,112,325 A | 5/1992 | Zachry |
| 5,188,126 A | 2/1993 | Fabian et al. |
| 5,190,059 A | 3/1993 | Fabian et al. |
| 5,329,944 A | 7/1994 | Fabian et al. |
| 5,664,582 A | 9/1997 | Szymaitis |

(Continued)

*Primary Examiner*—Daniel Wu
*Assistant Examiner*—Mark Rushing
(74) *Attorney, Agent, or Firm*—Kammer Browning PLLC (57) ABSTRACT

A system for tracking and locating surgical items and objects in an operating room environment that incorporates two-stage functionality. A first stage provides mechanisms for tracking objects using radio frequency (RF) tags that are positioned on or in conjunction with every surgical item and object so as to be tracked by a number of RF transceivers located about the operating room. In addition to integrating RF ID components, the tags integrate hard spherical components that are easily identifiable by ultrasonic detection. If an object is "lost" from the tracking system functionality (RF tracking), the system operator may review a last known location and movement path presented on a display and thereafter utilize an ultrasonic sub-system in a localized area to detect the exact location of the missing object or item. Narrowing the location of a "lost" object is facilitated by the use of one or more LED laser pointers that are directed through the last known path of the object and to its last known location.

18 Claims, 5 Drawing Sheets

U.S. PATENT DOCUMENTS

| | | |
|---|---|---|
| 5,923,001 A | 7/1999 | Morris et al. |
| 5,931,824 A | 8/1999 | Stewart et al. |
| 6,026,818 A | 2/2000 | Blair et al. |
| 6,447,294 B1 | 9/2002 | Price |
| 6,675,040 B1 | 1/2004 | Cosman |
| 6,687,531 B1 | 2/2004 | Ferre et al. |
| 6,777,623 B2 | 8/2004 | Ballard |
| 6,988,079 B1 * | 1/2006 | Or-Bach et al. ............... 705/28 |
| 7,001,366 B2 | 2/2006 | Ballard |
| 7,019,650 B2 * | 3/2006 | Volpi et al. ................ 340/572.1 |
| 7,251,352 B2 * | 7/2007 | Sauer et al. .................. 382/128 |
| 7,362,228 B2 * | 4/2008 | Nycz et al. ................ 340/572.1 |
| 2006/0181421 A1 * | 8/2006 | Forcier et al. ............ 340/572.1 |

* cited by examiner

SYSTEM FOR TRACKING SURGICAL ITEMS IN AN OPERATING ROOM ENVIRONMENT

CROSS REFERENCE TO RELATED APPLICATIONS

This application claims the benefit under Title 35 United States Code §119(e) of U.S. Provisional Application No. 60/783,096 filed Mar. 17, 2006, the full disclosure of which is incorporated herein by reference.

BACKGROUND OF THE INVENTION

1. Field of the Invention

The present invention relates generally to surgical systems, methods, and instrumentation. The present invention relates more specifically to systems for tracking and locating objects and items utilized during surgical procedures in operating room environments as well as real time visualization and location of foreign objects in the body while on the operating table.

2. Description of the Related Art

Surgical procedures typically require the use of a large number of small objects and items that both the physician and other attending healthcare providers must manipulate during the surgical procedure. Many of these objects and items, because of their function, find their way into the patient undergoing the surgical procedure, where they serve to control the flow of fluids within the surgical wound site or to retract tissue within the surgical opening for the overall purpose of facilitating the surgical procedure. In most instances these objects and items are removed from the surgical wound prior to the process of closing the wound after the surgical procedure has been completed. Despite numerous precautions, such surgical items and objects continue to be left within patients, generally for failure to have properly tracked and accounted for each of the items utilized in the surgery.

Many efforts have been made in the past to provide systems for locating items and objects that might have been left within the surgical wound during and after the surgical procedures have been carried out. Most of these efforts have focused on providing x-ray opaque material in or on the objects and items associated with the surgical procedure, such that they might readily be identified through an x-ray image of the surgical area post-surgery. There are however a number of drawbacks to such systems including the requirement of positioning x-ray equipment in conjunction with the surgical sight as well as inaccuracies in the visual review of an x-ray image to locate what are often poorly discernable object images. While metal based surgical instruments are generally opaque to x-rays and can easily be seen, many surgical implements such as sponges and many newer plastic based instruments must be made radio opaque to x-rays by the incorporation of threads (barium impregnated threads, for example) or the attachment of some type of radio opaque tag to the item.

The primary problem, however, with such systems that rely upon x-ray images to identify objects that may have been left within the patient is the simple requirement of positioning x-ray equipment in proximity to the patient in advance of closing the surgical wound. In many cases, even after going through the process of setting up for x-ray imaging, the objects of interest are sometimes not even seen within the often poorly defined image. Such x-ray equipment remains generally quite large and cumbersome and difficult to manipulate in conjunction with a patient on the operating table. In addition, any excess exposure to x-rays is known to have detrimental effects to the patient and to those within the immediate area unless proper shielding is maintained in place. For all of the above reasons, those systems that rely upon x-ray imaging techniques to detect items that may have been left within the surgical opening provide less than desirable solutions to the problem.

Some efforts have been made in the past to develop systems that utilize detection methods other than x-rays to locate and identify objects and items that may have been left within patients undergoing surgical procedures. These efforts have more recently focused on the utilization of ultrasound and radio frequency electromagnetic waves to locate items used in surgical procedures. Systems that rely strictly on ultrasound imaging suffer many of the same problems that are associated with x-ray imaging in that an inspection and interpretation of the ultrasound image is required in order to identify and locate tagged objects. Radio frequency based systems that utilize tags identifiable through RF transmissions are less dependent on image interpretation but suffer from an inability of RF waves to penetrate through more than a few centimeters of tissue. Some of the systems that have been developed in the past that address these various approaches to locating surgical objects and instruments include systems described in the following issued U.S. patents:

U.S. Pat. No. 3,834,390 issued to Hirsch on Sep. 10, 1974 entitled Combination Neurosurgical Sponge describes an early attempt to tag surgical sponges by positioning an x-ray detectable object together with each sponge and wrapping the sponge and x-ray marker together with a layer of porous material.

U.S. Pat. No. 4,114,601 issued to Abels on Sep. 19, 1978 entitled Medical and Surgical Implement Detection System describes a method by which surgical implements, surgical instruments, surgical sponges, and the like may be detected within the human body or other areas of interest by incorporating or adding a radio-frequency transponder. Non-linear mixing of two frequencies in a radio-frequency transponder is used. The transponder may be a small film deposition of ferrite material exhibiting gyro-magnetic resonance at selected frequencies or a solid state device exhibiting similar properties.

U.S. Pat. No. 4,193,405 issued to Abels on Mar. 18, 1980 entitled Detectable Medical and Surgical Implements describes a variety of surgical devices and implements that may be detected within the human body by incorporating a radio-frequency transponder therein. In this case, the transponder is described as being a small film deposition of ferrite material exhibiting gyro-magnetic resonance at selected frequencies, or a solid state device exhibiting similar properties.

U.S. Pat. No. 4,658,818 issued to Miller, Jr. et al. on Apr. 21, 1987 entitled Apparatus for Tagging and Detecting Surgical Implements describes a system for tagging and detecting a surgical instrument accidentally left within a patient by way of a miniature electrical oscillator attached to each implement. The oscillator is activated before surgery begins. The detection methods include use of a handheld RF receiver or the use of ECG electrodes and instruments.

U.S. Pat. No. 5,107,862 issued to Fabian et al on Apr. 28, 1992 entitled Surgical Implement Detector Utilizing a Powered Marker describes yet another modification of the above Fabian et al., this time incorporating a battery-powered marker (as opposed to an acoustic marker) and further incorporating an antenna with field generating means to generate an electromagnetic field and thereby provide the marker with signal identity.

U.S. Pat. No. 5,112,325 issued to Zachry on May 12, 1992 entitled Surgical Sponge with Plurality of Radio-Opaque Monofilaments describes a surgical sponge structure particularly for neuro-surgical applications comprising a fibrous web having attached to one surface thereof a locator string comprising a bundle of x-ray detectable monofilaments. This system anticipates the use of x-ray devices to scan for the presence of such surgical sponges during and post surgery.

U.S. Pat. No. 5,329,944 issued to Fabian et al. on Jul. 19, 1994 entitled Surgical Implement Detector Utilizing an Acoustic Marker describes a method and apparatus for accurately and reliably detecting surgical implements within animal or human tissue. The apparatus comprises a detector responsive to the presence, within a wound, of a surgical implement to which a marker is secured. The marker is adapted to produce identifying acoustic signal characteristics within the wound.

U.S. Pat. No. 6,026,818 issued to Blair et al. on Feb. 22, 2000 entitled Tag and Detection Device describes a method and a system for the detection of unwanted objects in surgical sites. These objects are described as including medical sponges or other items used in body cavities during surgery. The detection tag is of minimal size with a length of about 8 mm in the shape of a bead (ovate or circular) and is constructed of a medically inert material. Further, the bead incorporates a single signal emitter, such as the combination of a miniature ferrite rod, a coil, and a capacitor element embedded therein. Also described is an alternate embodiment wherein the tag includes a flexible thread composed of a single loop of wire and a capacitor element. A detection device is utilized to locate the tag by pulsed emission of a wideband transmission RF signal. The tag resonates with a radiated signal in response.

U.S. Pat. No. 6,675,040 issued to Cosman on Jan. 6, 2004 entitled Optical Object Tracking System describes a camera system operable in conjunction with data processors and graphic displays to provide tracking of instruments, objects, patients, and other devices in a surgical setting. The objective is primarily to provide the physician with a constructed view of the patient's anatomy in relationship to a variety of surgical instruments. The instrument "tags" comprise a wide variety of visually distinguishable markers associated with each of the instruments.

U.S. Pat. No. 7,001,366 issued to Ballard on Feb. 21, 2006 entitled Radiologically Trackable Surgical Sponges describes an operating room-wide system that employs radioopaque objects to count and account for surgical sponges. A container is structured to receive the surgical sponges and to be scanned by a radiation source (x-ray or the like) in a manner of counting the sponges as they are inserted into the disposal container. Connected computer systems are anticipated for maintaining the accounting records.

Efforts in the prior art have generally failed to realize a cost effective method for locating and tracking objects and instruments utilized in carrying out surgical procedures. Such systems developed in the past have proven to be less than desirable to implement, either because their implementation has been far too costly for the risks they seek to eliminate, or their implementation is far too cumbersome to carry out in connection with each and every surgical procedure within an operating room environment. The general problem as identified in the prior art is that very simple, easy to use systems, suffer from inaccuracy and unreliability; while reliable and accurate systems suffer from being overly complex and overly cumbersome to utilize.

It would be desirable, therefore, to have a system for tracking and locating objects and items utilized in surgical procedures that could carry out its functionality in a manner nearly transparent to the physicians and attending healthcare providers in the process of carrying out the surgical procedure. It would be desirable if much of the function of such a system could be carried out in automatic fashion such that interaction by the healthcare providers could be minimized. It would be desirable if a final check of the objects and items utilized in the surgical procedure would involve the review of a report from the system rather than the initiation of a locater function after the fact. It would be desirable if, at any point during the surgical procedure, attending healthcare providers could review the use and location of various items and objects and identify the mislocation or misplacement of any object earlier on in the surgical procedure.

It would be desirable if a system for locating and tracking objects and items utilized in surgical procedures integrated a two-stage process that resorted to focused location only when necessary. It would be desirable if, during the surgical procedure, items were tracked automatically by the system and only if any tracked items are "lost" during the surgical procedure, would a second stage in the process be implemented for isolating the location of the lost object and thereafter, through a much more narrowly focused identification process, locate the missing item so as to return it to a tracked status. It would be desirable if each of the above functions could be carried out in a system that was relatively unobtrusive to the surgical procedure and relatively cost effective to implement within the operating room environment.

SUMMARY OF THE INVENTION

In order to address the problems identified above in the prior art, the present invention provides a system for tracking and locating surgical items and objects in an operating room environment. The system incorporates two-stage functionality. A first stage provides a mechanism and method for accounting for and tracking objects from the point at which they enter into the operating room environment through their use in the surgical procedure, and finally to their anticipated removal from the surgical site. A second stage of the system involves mechanisms and procedures for locating items that may have been "lost" by the tracking system, through a combination of last known location and movement functionality with ultrasonic detection functionality in a localized area. The tracking system incorporates radio frequency (RF) tags that are positioned on or in conjunction with every item and object used in the surgical procedure that are identified and tracked by an array of radio frequency transceivers located about the operating room. The tags, in addition to integrating RF ID components, integrate hard spherical components that are easily identifiable by ultrasonic detection. If an object is "lost" from the tracking system functionality (RF tracking), the system operator may review a last known location and movement path presented on a display and thereafter utilize an ultrasonic sub-system in a localized area to detect the exact location of the missing object or item.

The RF tracking system of the present invention utilizes a specialized tag that is not only identifiably by RF transmissions, but which further reflects a signal that is discretely identifiable as having come from a specific tag and therefore from a specific item or object being used. The items and objects thus tagged within the tracking system are identified and their positions are displayed both in table format and in visual format in conjunction with a live video image of the operating room environment. The RF tags are positioned on a miniature substrate that is easily attachable to any and all of the various objects and items typically used in conjunction with surgical procedures.

The second stage process of the present invention, namely that of locating items that have fallen from the tracking function, involves a number of additional functionalities associated with the RF system as well as an ultrasonic detection system for locating a specific object in a focused, confined area. The RF tracking system alerts the operator to any objects or items that have fallen out of the tracking system, typically due to their placement within the patient out of range of the penetration of the radio frequency waves. When such occurs, the operator may take one of two additional actions to assist in the location of the missing object or item. First, the user may trigger the system to identify and display the last ten (10) seconds of known and tracked motion for the object that is now missing. Typically this would take the form of a traced path on a video image of the operating room showing the movement of the object immediately prior to the point in time where is was dropped from the tracking system.

A second functionality of the system designed to assist the operator in locating dropped objects and items, involves one or more LED laser pointers fixed to pointing mechanisms, again positioned in various locations around the operating room environment. In conjunction with the video image of the motion of the object, the LED laser pointer mechanisms would each point to the last know location of the object to further localize and narrow the focus of the search.

A final step in the process of locating a missing object, involves the use of a portable, hand-held ultrasonic transducer that may be brought to the location identified by the tracking system as the last known location of the object, such that the ultrasound detection functionality may produce an image that easily identifies the ultrasonic tag component and thereby identifies the location of the tagged object, typically within the surgical site on the patient.

Other objects of the present invention will become apparent to those skilled in the art from the following detailed description of the invention when read in conjunction with the various drawing figures attached.

DETAILED DESCRIPTION OF THE PREFERRED EMBODIMENTS

Figure 1:
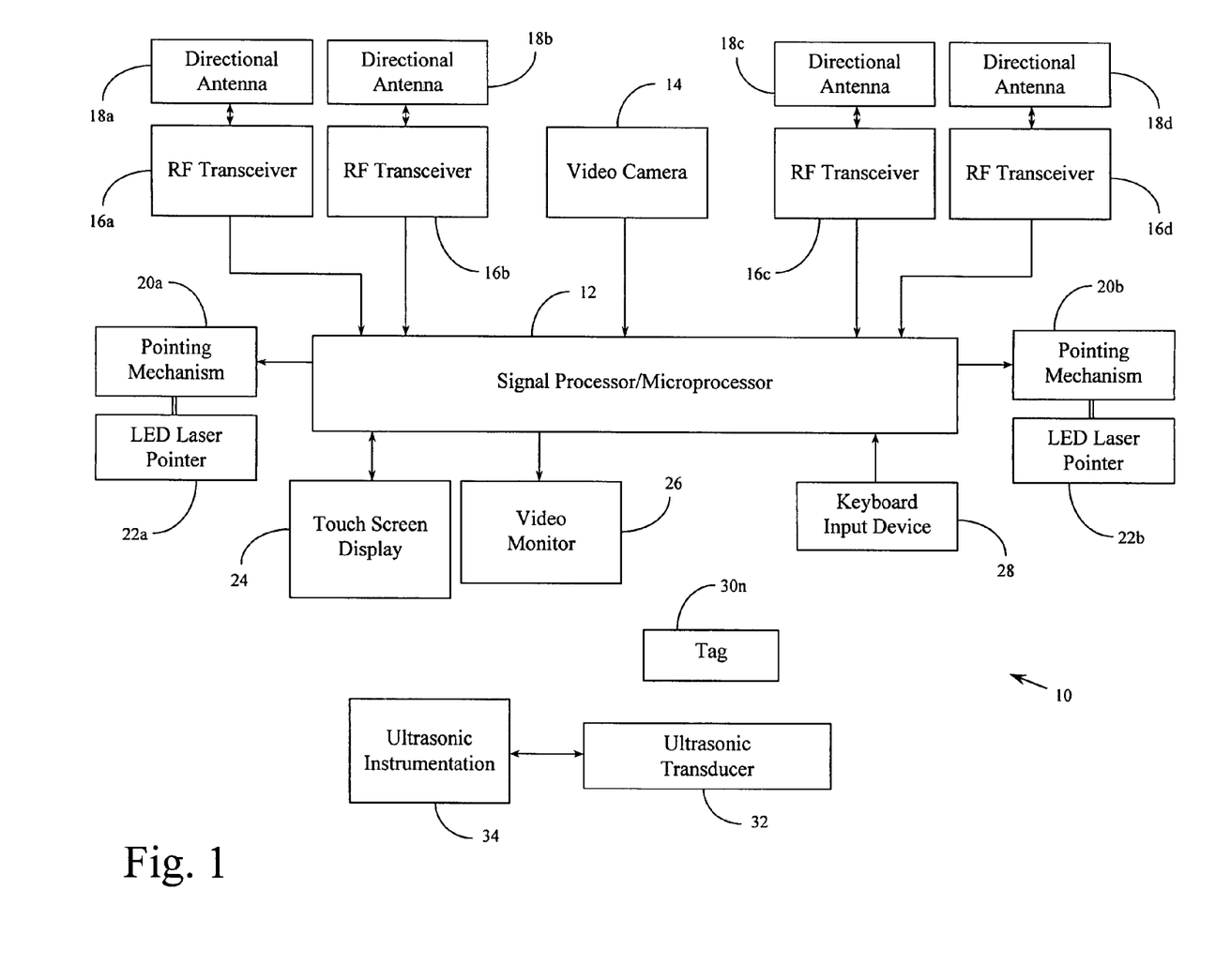
FIG. 1 is a functional block diagram showing the various components of the system of the present invention and their functional relationships to each other.

Reference is made first to FIG. 1 for a description of the overall system of the present invention and the various components that makeup the system and its functional operation. FIG. 1 is a schematic block diagram wherein each of the components are represented by a module connected to a central controller associated with the overall operation of the system. The numbering and positioning of each of the components of the system as shown in FIG. 1 are only generally associated with their physical location within the system. The actual physical structure of a typical implementation of the system is presented in greater detail in association with FIG. 2.

Tracking system 10, as shown in FIG. 1, is centered around signal processor/micro processor 12 which, in the preferred embodiment of the present invention, may simply be a PC structured with the appropriate data input and output ports for operation in conjunction with the various components of the system. In general, signal processor/microprocessor 12 receives input from an array of components and directs output to a variety of display devices as well as controlling a number of pointing mechanisms for operation of the system. In particular, microprocessor 12 receives input on the various RF tags 30n utilized within the system by way of an array of directional antennas 18a-18d and RF transceivers 16a-16d. As described in more detail below, this array of antennas and RF transceivers may number from one to as may as three or four, and are positioned in a variety of elevated locations throughout the operating room environment. FIG. 1 shows the preferred embodiment wherein four sets of directional antenna/RF transceiver components are each configured to provide input to microprocessor 12.

Additionally providing input to microprocessor 12 is video camera 14 which in conjunction with the RF tracking function of the system of the present invention provides the ability to display tag locations within a visual image of the operating room itself. Also positioned within the operating room and connected to the signal processor/microprocessor 12 are one or more pointing mechanisms 20a & 20b operable in conjunction with one or more LED laser pointers 22a & 22b. In a manner described in more detail below, these pointing mechanisms facilitate the locating of a tag if it is lost from the RF tracking function of the system. Microprocessor 12 controls the operation of pointing mechanisms 20a & 20b and therefore is capable of directing the light beams from LED laser pointers 22a & 22b.

The human interface with the system of the present invention as shown in FIG. 1 is provided primarily through touch screen display 24, video monitor 26, and an optional keyboard input device 28. Touch screen display 24 is used primarily to provide ongoing status reports of the tracked location of the tagged surgical objects and items. It also provides the means for the operator to activate the laser pointer functionality of the system and to activate the last motion tracking functionality of the system. These operations are described in more detail below. Keyboard input device 28 provides a mechanism for entering data into the system such as patient and event data as may be desired for a record of the surgical procedure.

The balance of tracking system 10 comprises ultrasonic instrumentation 34 and the associated ultrasonic transducer 32. The ultrasonic components of this system may be stand alone components as shown in FIG. 1 or may be integrated into the microprocessor based system described above. In other words, the display associated with the ultrasonic components may be self-contained within ultrasonic instrumentation 34 (as is typical for a small ultrasound system), or may be connected through microprocessor 12 to video monitor 26 or touch screen display 24 to provide the visual ultrasonic image display.

Figure 2:
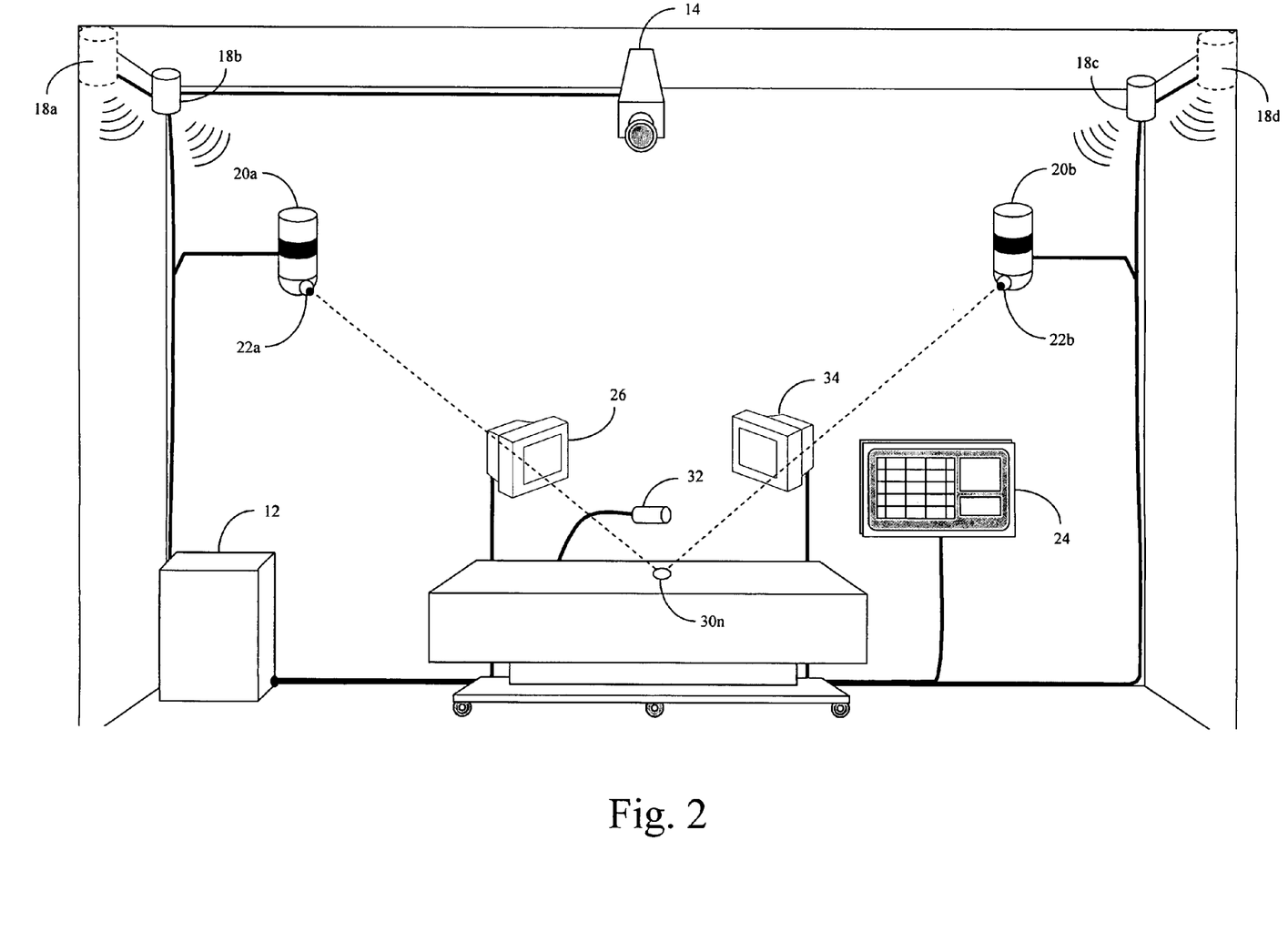
FIG. 2 is a schematic prospective view of the system of the present invention in a typical installation within an operating room environment.

Reference is now made to FIG. 2 for a more detailed description of the operation of the system of the present invention and the structural arrangements of the various components within an operating room environment. FIG. 2 shows a typical operating room environment centered on an operating table around which are positioned both the components of the system of the present invention and other necessary instruments and components for carrying out the surgical procedure. An example of a tag 30n is shown in FIG. 2 as positioned at a point on the operating table that may be typical of the placement of a surgical object or item, such as a surgical sponge within the patient. As indicated in the objectives of the present invention, most of the operation of the tracking system is intended to be transparent to the physician and attending healthcare providers. For this reason, most of the components of the system are arrayed about the operating room in an unobtrusive manner. Directional antennas 18a-18d are positioned (for example) in the corners of the room near the ceiling so as to provide unobstructed RF transmission paths to the tags being utilized. The RF transceivers themselves (not shown in this view) may be integrated into the antenna devices positioned as shown, or may simply reside within the enclosure housing microprocessor 12.

Also positioned in an elevated location within the operating room is video camera 14. The placement of this video imaging device is likewise intended to provide an unobstructed view of the patient on the operating table so as to serve as a means for imaging the probable locations of tagged objects within the view.

The combination components comprising pointing mechanisms 20a & 20b each associated with corresponding LED laser pointers 22a & 22b, are further placed in position to provide direct line-of-sight access to the most likely placement of tagged objects within the operating room environment. Each of the above described and positioned components is connected by appropriate electronic cabling to microprocessor 12 which, in the preferred embodiment, is contained within a cabinet enclosure typically positioned to one side in the operating room or perhaps even contained within a movable cart. If movable, it is preferable for the connections to the various components described to be likewise removable from the instrumentation within the cart. Alternately, the various components could each retain wireless capabilities for communicating with the microprocessor 12 contained within the cabinet enclosure positioned at floor level within the operating room. Typical short range digital communication devices are well known in the art that would allow the placement and positioning of the various components shown in FIG. 2 without the need for running electronic cabling to the devices. Such devices would then require battery systems to maintain power but would otherwise be more easily installed and implemented in conjunction with the present system.

Positioned at eye level within the operating room environment are the various display components to complete tracking system 10. Touch screen display 24 would, in the preferred embodiment, typically be a flat panel LCD or plasma type display screen that integrated touch screen capabilities. This screen would typically be mounted to the wall adjacent the operating table or could be hung from the ceiling or mounted to a bracket on the wall so as to position the display in the most accessible manner. The remaining two displays shown in FIG. 2, namely video monitor 26 and ultrasonic instrumentation monitor 34, are likewise positioned either on support brackets extending from the wall or hangers extending from the ceiling in the operating room. In any case, the various displays may also be positioned on a movable cart associated with the cabinet enclosure housing microprocessor 12. In this manner, the entire system of the present invention may be moved to and from the specific operating room as needed.

Video monitor 26 is generally intended to be utilized in conjunction with the RF tracking functionality of the system of the present invention, while monitor 34 is shown as might be utilized in conjunction with ultrasonic transducer 32 to provide the ultrasonic locating functionality of the system. As indicated above, the function of these two monitors may in some embodiments of the invention be combined into one monitor. Likewise the video display functionality associated with both of these components (RF tracking and ultrasonic) may be displayed in a screen-in-screen functionality associated with flat panel touch screen display 24.

Figure 3A:
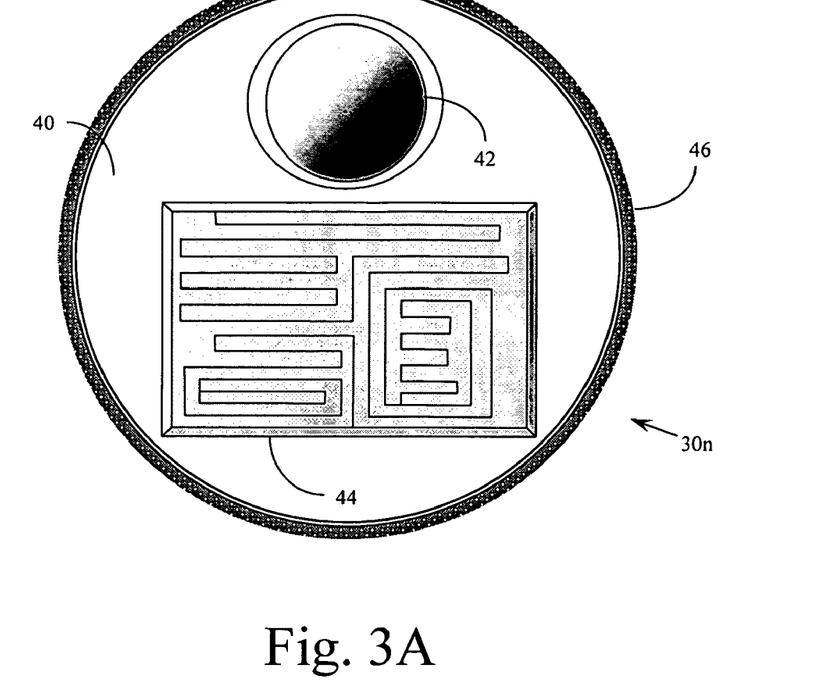
FIG. 3A is a top plan view of a typical tag configuration operable in association with the system of the present invention.
Figure 3B:
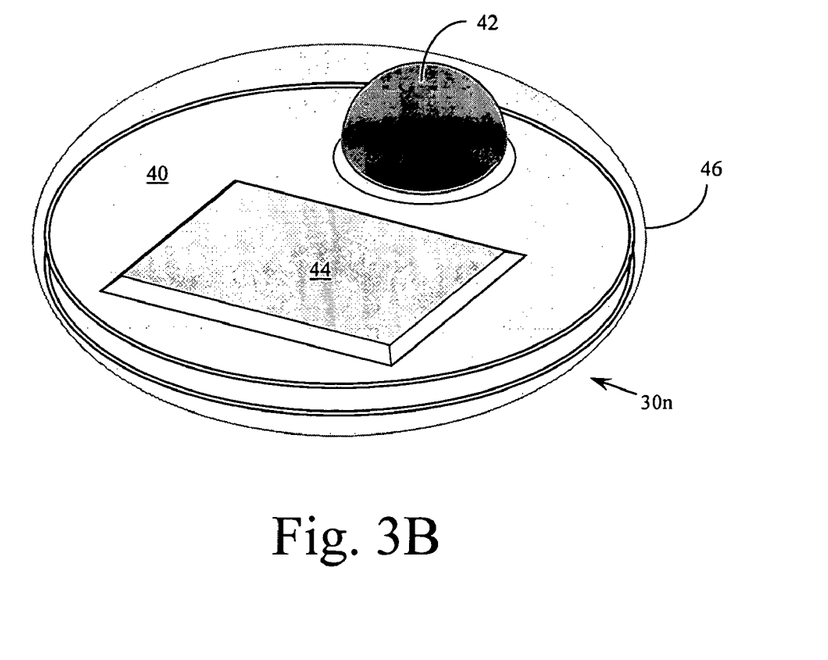
FIG. 3B is a perspective view of the tag shown in FIG. 3A.

Reference is now made to FIGS. 3A & 3B for a brief description of the structure of a tag, bearing elements suitable for operation in conjunction with the above described system. Tag 30n (as an example) has two primary functional elements; hard sphere 42 and RF ID antenna/circuit 44. Each of these elements is positioned on and adhered to tag substrate 40. The entire assembly is surrounded by a plastic coating 46. Hard sphere 42, in the preferred embodiment, may comprise a simple ceramic or steel sphere having a density appropriate for providing a strong acoustic echo for an ultrasonic pulse that encounters the sphere. In this manner the hard sphere allows the ultrasonic detection components of the system of the present invention to readily disclose the location of the tag and therefore the location of the tagged object or item.

RF ID antenna/circuit 44 is a small circuit chip that provides a unique RF signal identifier for the item to which the tag is attached. Technologies are known in the art to provide not only circuits capable of reflecting RF signals transmitted to them, but to reflect such a signal in a manner that readily identifies the circuit and therefore the specific tag, as by a number association or the like, with database stored and referenced RF reflective characteristics. In other words, the various RF ID antenna/circuits 44 positioned in conjunction with tag 30n would each be slightly different in configuration so as to return a reflected RF signal to the RF transceivers that not only locates the tag and the object, but identifies it as distinct from various other tagged objects and items being utilized within the system.

Figure 4:
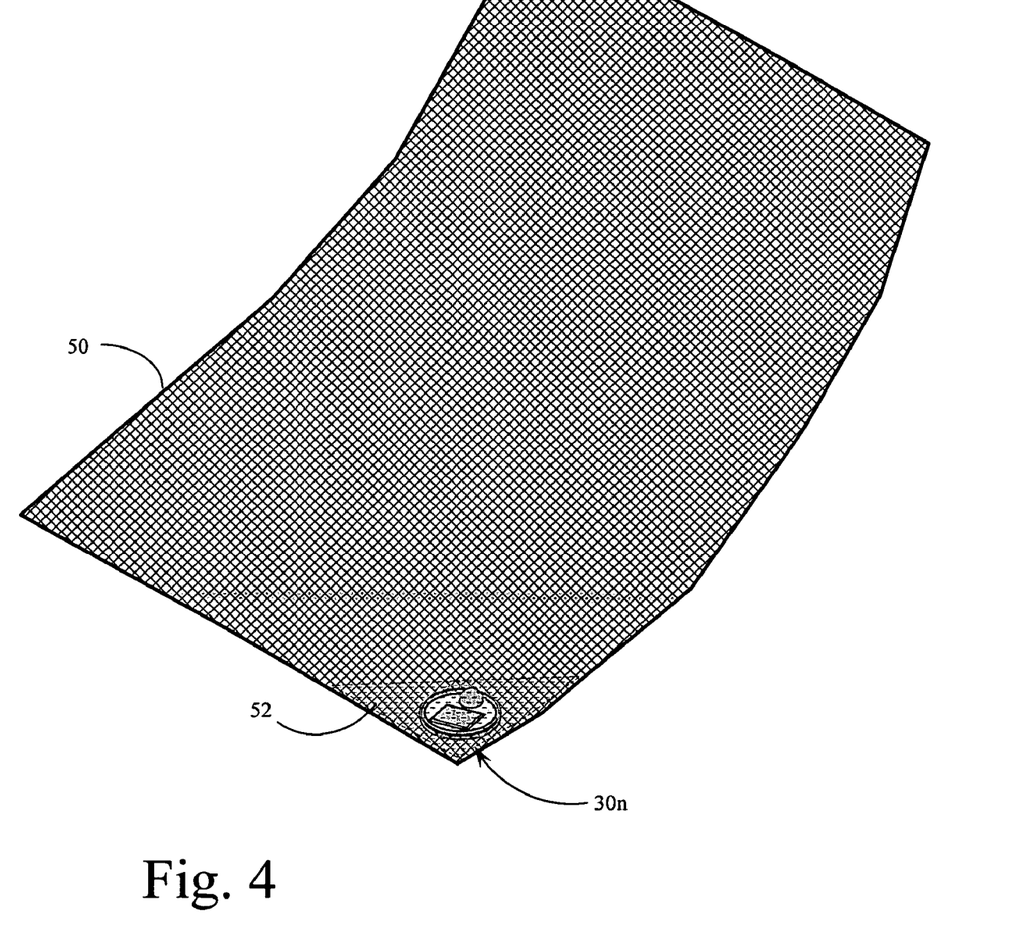
FIG. 4 is a perspective view of a typical attachment of a tag of the present invention to a surgical item (in this case, a surgical sponge).

The combination tag comprising the substrate 40, hard sphere 42, and antenna/circuit 44 is covered over with plastic coating 46 that in the preferred embodiment comprises a sterile, non-reactive plastic coating with an acoustic impedance similar to blood or saline solution, in a manner that allows and enables acoustic energy to readily penetrate the coating. The functionality and the process for tracking and locating the tag and its attachment to a surgical object or item is described in more detail below. FIG. 4 provides but a single example of the manner in which tag 30n may be attached to a surgical object or item. In this case, surgical sponge 50 incorporates a tag pocket 52 into which locator tag 30n may be adhered or sewn. In this example, a simple corner piece of surgical sponge material is positioned over tag 30n and adhered around its edges to the primary structure of surgical sponge 50.

A variety of other mechanisms for attaching tag 30n to the large variety of surgical objects and instruments typically utilized can readily be realized by those skilled in the art from an understanding of the example shown in FIG. 4. Any fabric objects, such as surgical sponges and the like, could either integrate the pocket configuration shown in FIG. 4 or could simply receive an inert adhesive that would bond tag 30n to the fabric material. For other objects that may be solid, such as plastic clamps or forceps and the like, the small tag may be adhesively bonded to a flat portion of the object or may be secured to the object through a short cord or filament.

It is also anticipated that the circular, disc-like configuration of locator tag 30n shown in FIGS. 3A & 3B might change according to the specific surgical objects or items to which it is to be attached. In some instances a long, narrow tag may be preferable to the circular tag configuration shown in these examples. Those skilled in the art will recognize that modifications to the geometry of the tag so as to fit the variety of surgical objects and items being utilized, may result in a variety of geometric configurations.

Reference is now made again to FIGS. 1 & 2 for a description of the functionality of the system of the present invention and the typical manner in which it may be utilized in the process of carrying out a surgical procedure. Once again, the goal of the system is to maintain positional information and to provide real time unambiguous indications of the location of a set of medical supplies, each of which incorporates a tag of the type that provides both radio frequency (RF) and ultrasonic indications. The typical example of the utilization of such a tag would be to provide a device that tracks the use of surgical sponges in an operating room environment, although the system is intended to have wider application to become a general aid to maintaining positional awareness of virtually any item or object in the operating room environment.

As indicated above, each item to be tracked (for example, surgical sponges and the like) will have a special tag (described above) attached to or embedded in it. In the preferred embodiment, this tag will be about the size of a U.S. dime and will incorporate the two primary elements described above. These include an RF ID antenna/circuit that provides the unique identifier for the item and one or more small hard spheres (ceramic or steel) to provide a strong acoustic echo for an ultrasonic pulse. The RF ID antenna/circuit and the hard spheres are encapsulated in a sterile, non-reactive plastic coating that permits both RF waves and ultrasonic waves to penetrate to the functional elements of the tag.

It is anticipated that the RF transceivers of the preferred embodiment of the system of the present invention would comprise commercial grade RF transceivers that are mounted in the corners of the room (see FIG. 2) to provide the real time tracking functionality for each of the medical items while they are external to the patient and while they are internal to the patient up to a 20 cm depth. Radar tracking type algorithms using the RF ID tags as reflective beacons are associated with the transceivers in a manner that allows not only the identification of the RF ID tags within the system, but a degree of triangulation and location tracking based upon signal strength and direction. Transceiver systems operable in conjunction with radar detection equipment are available which will allow the processing of signals as small as −117 dB. As indicated above, these transceiver systems would not only be capable of identifying the presence of specifically configured tags within the operating room, but would also be able to triangulate their location by way of the placement of multiple antennas (and multiple transceivers) at elevated positions within the operating room (see FIG. 2).

Figure 5:
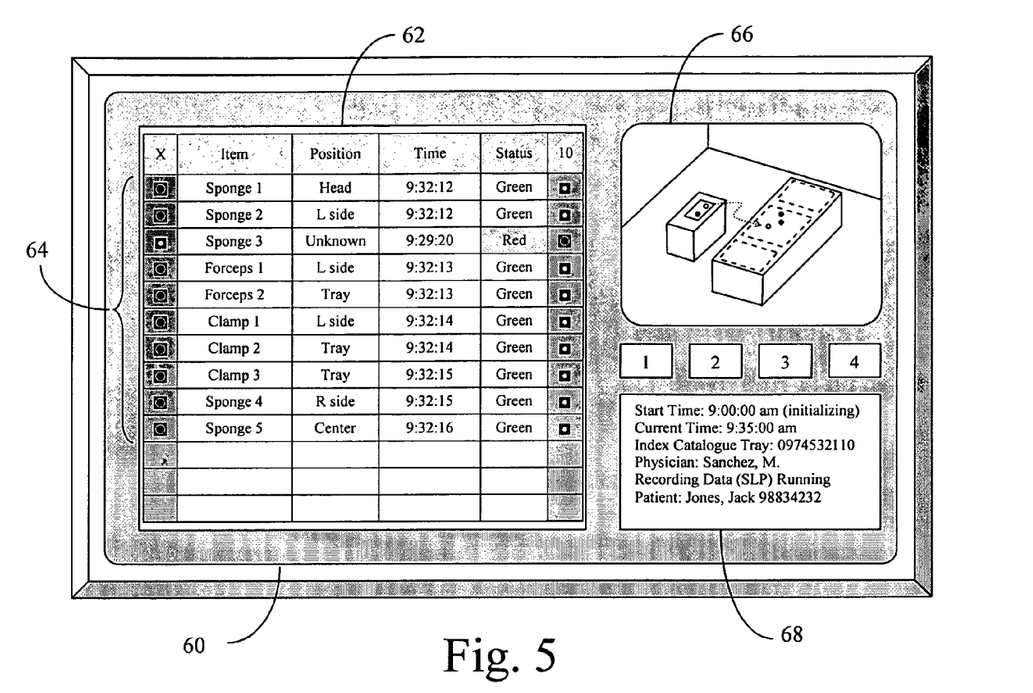
FIG. 5 is a detailed view of a typical touch screen display operable in association with the system of the present invention.

As tagged objects are introduced into the operating room environment, they are identified, counted, and located by the RF tracking system and incorporated into a record keeping system that is continuously updated and displayed to the healthcare personnel within the operating room. The transceivers described above communicate the location information they have gathered into a central computer system that is connected to the touch screen display positioned near the healthcare personnel. This touch screen display comprises a monitor that displays the operating room layout as well as a data table logging each of the items being tracked along with relevant information associated with the items. Table 1 shown below, as well as shown in FIG. 5, provides an example of the type of information displayed on the touch screen panel display. Also provided on this panel display, in addition to the information mentioned above, are touch screen "buttons" integrated into the data table that allow the user to activate two additional functional elements of the system of the present invention. To one side of the table, a number of such touch screen buttons allows the user to activate the LED pointer system, while a similar column of touch screen buttons on the opposite side of the data table allow the user to activate the last location path functionality of the system.

It may be desirable to introduce the various objects to be utilized during the surgical collectively in advance of the start of the procedure. Each object may then be "introduced" into the system, identified, counted, and located prior to movement into proximity to the patient. Such an initial "count" may help prevent an inaccurate introduction of an object that might be obscured from the "view" of the RF antennas if introduced during the operation. In this manner a count of all objects (or of each object in a number of different categories) may be initially acquired and provided to operating room personnel through the various display means described. Such an initial count scan may be carried out with the described RF antenna positioned about the operating room, or may be carried out with a lower level (about waist high) RF scanner under which the objects may be passed as they are introduced into the room.

TABLE 1

| Laser On | Item | Position | Time | Status | Last 10 sec |
| --- | --- | --- | --- | --- | --- |
| [ ] | Sponge #1 | Near Head | 9:32:12 | Green | [ ] |
| [ ] | Sponge #2 | L Side | 9:32:12 | Green | [ ] |
| [ ] | Sponge #3 | Unknown | 9:29:20 | Red | [ ] |

Once the surgical items and objects are identified, counted, and catalogued by the system by way of the RF ID tag components, they are continuously tracked throughout the surgical procedure. The identity of the object, its current location (as optionally displayed information), the time of its last identification, and the current status of its location, are all provided on the display. Any item or object that is not within the tracking system, i.e., not within the view of the RF tracking functionality, is displayed as a "red" status on the display and the time of its last observation is provided. In this manner the user may easily activate the LED laser pointer system by touching the touch screen display "button" next to that particular item to direct the system to point to its current or last known position. This function instructs the system to activate (and thereafter deactivate) the LED laser pointers for the particular item shown in the table.

In a similar fashion, the "last ten (10) second" column of touch screen buttons will instruct the system to activate the LED laser pointers and to display the last ten (10) seconds of movement from any known positional data for that particular item. Ten seconds of movement is typically sufficient to allow the user to visualize on the display, and with the assistance of the LED laser pointers, to localize and focus an area of investigation sufficiently to allow utilization of the ultrasonic functionality of the system. Other time periods may be utilized depending upon the specific items of concern, their manner of use in the surgical procedure, and their anticipated placement within the surgical site. As indicated, the last motion of an object may be represented by either or both of the LED laser tracking system, or the visual display system based on the RF tracking. Both FIG. 5 & FIG. 6 show the manner in which the visual display of the motion track may be carried out.

FIG. 5 represents a typical display associated with the touch screen monitor of the system of the present invention. In FIG. 5 display presentation 60 represents the standard ongoing display programmed to be provided on the touch screen display 24 of the system of the present invention. As an example of the kind of information provided in this manner, touch screen presentation 60 shows a number of various display elements. These display elements include item location table 62b, locate buttons 64 (described above), and an optional screen-in-screen video display 66. Additional event information and data may be provided in the form of text on event information display 68.

As described above, item location table 62 comprises information on each of the items (sponges, forceps, clamps, etc.), their general position within the operating room (location on the patient or on a tray table to the side of the operating table), the approximate time of the last location of the item, and the item status as either "green" (known and being tracked) or "red" (unknown and requiring location). A first column of touch screen buttons represented by "X" in FIG. 5 comprises locate buttons 64 which are intended to activate the LED laser pointers of the system. A second column of touch screen buttons in table 62 comprises means for activating the last ten (10) second motion display for each of the identified items, again as described above. This information is then shown on either or both of screen-in-screen video display 66 within touch screen presentation 60 or as described below in conjunction with FIG. 6 on video monitor screen presentation 70.

Figure 6:
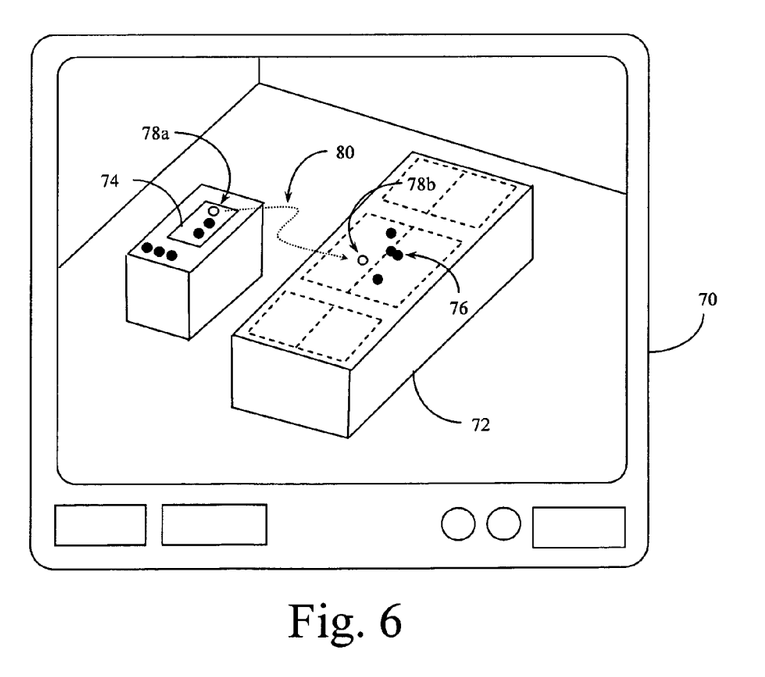
FIG. 6 is a detailed view of a typical video display screen operable in conjunction with the system of the present invention.

Video monitor screen presentation 70 shown in FIG. 6 may represent either the same screen-in-screen video display 66 shown in FIG. 5 or may represent a stand alone video monitor positioned adjacent the operating table within the operating room. As the display would suggest, the primary feed for the video shown is that of video camera 14 described above and positioned in such a location as to provide an overview image of the operating room environment. On video monitor screen presentation 70 can be seen operating table 72 and an adjacently positioned surgical tray 74. A variety of known location tagged items 76 are identified on the screen and are characterized in a manner distinct from those items whose locations are unknown. Unknown location tagged items 78a-78b may for example be identified on video monitor screen presentation 70 by red dots while known location tagged items 76 may be identified by green dots. In the example shown on video monitor screen presentation 70 an effort is being made (for example) to locate an unknown location tagged item 78a-78b and includes the ten second path image 80 that has been generated by the system to facilitate the user in locating the unknown location object.

The view example shown in FIG. 6 therefore provides the position of the unknown location tagged item at a point ten seconds prior to its "disappearance" at 78a while also providing its last identified position at 78b. In this manner, ten second path 80 assists the user in localizing the area within which an ultrasonic investigation might beneficially be carried out. As indicated above, this visual display operable in conjunction with the progressive movement of the LED laser light beams provides all of the narrowing and focusing of the area to be searched necessary to permit full functionality of the ultrasonic components of the system.

It will be recognized from the above description that operation of the various functional components of the system of the present invention may be carried out as the surgical procedure progresses and/or immediately prior to closure of the surgical wound after the critical activities in the surgical procedure have been carried out. The availability of personnel to monitor the tracking carried out by the system may determine whether the locating functionality is initiated either during the surgical procedure or prior to closing. The display systems and software functions described above are capable of being carried out under any such scenario. From a simple counting functionality to the more complex tracking and locating functionalities described above, the display systems and software of the present invention may adapt to the degree of attention that operating room personnel are able to direct to the monitoring system.

It may be anticipated, for example, that certain surgical items such as sponges, may "disappear" from the RF tracking system of the invention as a matter of course and therefore may be expected to show a status of red being in an "unknown" position during some part of the surgical procedure. It would be important to locate these objects only prior to closing the surgical site on the patient rather than necessarily interrupting the surgical procedure simply to verify that these objects are in fact positioned within the patient at a depth beyond the reach of the RF tracking system. It is recognized, however, that at such point in time that the surgical procedure has been completed, but before closing of the surgical opening, a visual inventory of the items utilized can be quickly and readily obtained from a view of the touch panel display described above. All objects identified with a "red" status can thereafter be located by pressing the appropriate touch screen button to activate either or both of the LED laser pointer locator functionality or the visual display last ten second motion locator functionality. In either case, if the location of any object remains unknown, and therefore is characterized by a "red" status, the healthcare providers may use the present system to isolate the last known location of the object, and thereafter utilize the ultrasonic components of the system of the present invention to specifically identify where the object is positioned such that it may be removed and thereafter returned to the RF tracking system log.

The ultrasonic components of the system of the present invention may utilize off-the-shelf type instruments and transducers as the hard sphere components of the locator tags of the present system are intended to provide a more than adequate return when an ultrasonic wand device (transducer) is scanned over the region previously identified and focused on. The hard spheres would thereby reflect brightly and show up unambiguously in the ultrasonic image displayed in any of the manners described above. This would therefore allow the operating team to locate and remove the item prior to closing the surgical site.

The advantages to the above described system over existing protocols should now be apparent. Currently, if a sponge count, for example, indicates that a surgical sponge is missing at a point in time when a surgical site is about to be closed, and the surgical sponge is not readily located, the operating room team will typically take an x-ray of the patient and look for either barium embedded in the surgical sponge or other x-ray opaque objects attached to the surgical sponges. The system of the present invention eliminates the need to rely upon x-ray equipment by providing the two stage tracking and then locating approach to maintaining control over the various objects and items typically utilized in surgical procedures.

Although the present invention has been described in terms of the foregoing preferred embodiments, this description has been provided by way of explanation only, and is not intended to be construed as a limitation of the invention. Those skilled in the art will recognize modifications of the present invention that might accommodate specific operating room environments and certain specific surgical requirements. Such modifications as to system components, system size, and even configuration, where such modifications are merely coincidental, do not necessarily depart from the spirit and scope of the invention. It is anticipated that significant variations may occur, for example, in the configuration of the tag utilized in conjunction with the system of the present invention. As long as the RF and ultrasonic detection elements are present in the tag, the configuration of the tag and the manner with which it is attached to the surgical object or item may vary. Likewise, the number, arrangement, and placement of the various components within the system may vary according to the specific configuration of the existing operating room. Again, all of these various modifications and variations do not necessarily depart from the spirit and scope of the invention.

We claim:

1. A system for tracking and locating medical utility items within a surgical environment, the system comprising:
   (a) a plurality of tags, at least one tag associated with each medical utility item to be tracked, each tag comprising a radio frequency (RF) responsive element and an ultrasonic responsive element;
   (b) at least one RF transceiver positioned within the surgical environment and for transmitting an RF signal to, and receiving an RF signal back from, the RF responsive element of each tag, the RF transceiver thereby tracking the locations of the tags, the RF transceiver further outputting signal information comprising the locations of the tags;
   (c) a microprocessor receiving the signal information from the at least one RF transceiver and maintaining a log of the locations of the tags and determining if and when a tag is not being RF tracked by the RF transceivers;
   (d) at least one display device associated with the microprocessor for displaying the log of the locations of the tags and for alerting a user if and when a tag is no longer being RF tracked, the at least one display device further for displaying at least one last known location of a tag that is no longer being RF tracked; and
   (e) at least one ultrasonic transducer positioned within the surgical environment and for transmitting ultrasonic waves to, and receiving ultrasonic waves back from, the ultrasonic responsive element of each tag within a localized space associated with the at least one last known location of a tag that is no longer being RF tracked.

2. The system of claim 1 further comprising at least one pointing mechanism for being controlled by the microprocessor, the at least one pointing mechanism comprising a light source and a movable support, the microprocessor controlling the at least one pointing mechanism to point to the at least one last known location of a tag that is no longer being RF tracked.

3. The system of claim 2 wherein the light source comprises a collimated light source for projecting a narrow beam of light in a specified direction.

4. The system of claim 1 wherein the at least one RF transceiver comprises a directional RF receiver for outputting at least azimuthal orientation information regarding the locations of the tags.

5. The system of claim 1 wherein the at least one RF transceiver comprises at least one RF scanner/counter positioned to detect and count each of the medical utility items to be tracked as they are introduced into the surgical environment.

6. The system of claim 1 wherein the at least one RF transceiver comprises at least three RF transceivers, the at least three RF transceivers for triangulating the return RF signals from the tags.

7. The system of claim 1 wherein the plurality of tags each further comprise a support substrate and an encapsulating material, the RF responsive element and the ultrasonic responsive element each positioned on and supported by the support substrate and encapsulated therewith by the encapsulating material, the encapsulating material comprising a material that is generally transparent to the RF signal and to the ultrasonic waves.

8. The system of claim 1 wherein the RF responsive element of each of the plurality of tags comprises a distinct identification characteristic, said identification characteristic for being represented in the return RF signal traveling back from the tag to the RF transceiver and thereby identifying the tag and the medical utility item to which the tag is attached as apart from the balance of the items with tags.

9. The system of claim 8 wherein the distinct identification characteristic of each of the plurality of tags is previously stored in a data storage device associated with the microprocessor.

10. The system of claim 1 wherein the at least one display device further comprises a touch screen display for receiving touch input from a user, the touch input comprising an instruction to initiate the display of the at least one last known location of a tag that is no longer being RF tracked.

11. The system of claim 1 wherein the at least one last known location of a tag that is no longer being RF tracked comprises a time-sequence of a plurality of last known locations of a tag that is no longer being RF tracked.

12. The system of claim 11 wherein the time-sequence of a plurality of last known locations of a tag that is no longer being RF tracked comprises a set of last known locations over a selectable period of time.

13. The system of claim 1 further comprising a video imaging device operable in conjunction with the microprocessor to provide an image of the surgical environment, the image of the surgical environment for display on the at least one display device and facilitating the display of the at least one last known location of a tag that is no longer being RF tracked.

14. The system of claim 1 wherein the at least one display device comprises a first display device and a second display device, the first display device comprising a flat panel touch screen display device for displaying the log of the locations of the tags and the second display device comprising a device for displaying the at least one last known location of a tag that is no longer being RF tracked.

15. The system of claim 13 wherein the at least one display device comprises a first display device and a second display device, the first display device comprising a flat panel touch screen display device for displaying the log of the locations of the tags and the second display device comprising a device for displaying the at least one last known location of a tag that is no longer being RF tracked superimposed on the image of the surgical environment.

16. The system of claim 1 wherein at least one of the plurality of tags is attached to a medical utility item by enclosing the tag within a pocket formed on the medical utility item.

17. The system of claim 1 wherein at least one of the plurality of tags is attached to a medical utility item by adhering the tag to the medical utility item with a medically inert adhesive.

18. A system for tracking and locating medical utility items within a surgical environment, the system comprising:
   (a) a plurality of tags, at least one tag associated with each medical utility item to be tracked, each tag comprising a radio frequency (RF) responsive element and an ultrasonic responsive element;

(b) at least one RF transceiver positioned within the surgical environment and for transmitting an RF signal to, and receiving an RF signal back from, the RF responsive element of each tag, the RF transceiver thereby tracking the locations of the tags, the RF transceiver further outputting signal information comprising the locations of the tags, the RF responsive element of each of the plurality of tags further comprising a distinct identification characteristic, said identification characteristic for being represented in the return RF signal traveling back from the tag to the RF transceiver and thereby identifying the tag and the medical utility item to which the tag is attached as apart from the balance of the items with tags;

(c) a microprocessor receiving the signal information from the at least one RF transceiver and maintaining a log of the locations of the tags and determining if and when a tag is not being RF tracked by the RF transceivers;

(d) at least one pointing mechanism for being controlled by the microprocessor, the at least one pointing mechanism comprising a light source and a movable support, the microprocessor controlling the at least one pointing mechanism to point to the at least one last known location of a tag that is no longer being RF tracked;

(e) at least one display device associated with the microprocessor for displaying the log of the locations of the tags and for alerting a user if and when a tag is no longer being RF tracked, the at least one display device further for displaying at least one last known location of a tag that is no longer being RF tracked;

(f) a video imaging device operable in conjunction with the microprocessor to provide an image of the surgical environment, the image of the surgical environment for display on the at least one display device and facilitating the display of the at least one last known location of a tag that is no longer being RF tracked; and (g) at least one ultrasonic transducer positioned within the surgical environment and for transmitting ultrasonic waves to, and receiving ultrasonic waves back from, the ultrasonic responsive element of each tag within a localized space associated with the at least one last known location of a tag that is no longer being RF tracked.

* * * * *